(12) United States Patent
Polo Pozo et al.

(10) Patent No.: US 9,394,356 B2
(45) Date of Patent: Jul. 19, 2016

(54) NUTRITIONAL SUPPLEMENT, METHOD FOR INCREASING THE BACTERIAL MASS IN THE RUMEN OF A RUMINANT AND NUTRITIONAL PREPARATION AND CORRESPONDING USES

(75) Inventors: Francisco Javier Polo Pozo, Barberà del Vallès (ES); Carmen Rodriguez Canel, Barcelona (ES); Alejandro Bach Ariza, Sant Cugat del Vallès (ES); Anna Aris Giralt, Sant Cugat del Vallès (ES)

(73) Assignee: APC EUROPE S.A., Barcelona (ES)

( * ) Notice: Subject to any disclaimer, the term of this patent is extended or adjusted under 35 U.S.C. 154(b) by 0 days.

(21) Appl. No.: 14/131,098

(22) PCT Filed: Jul. 6, 2012

(86) PCT No.: PCT/ES2012/000188
§ 371 (c)(1),
(2), (4) Date: Jan. 6, 2014

(87) PCT Pub. No.: WO2013/004865
PCT Pub. Date: Jan. 10, 2013

(65) Prior Publication Data
US 2014/0171360 A1 Jun. 19, 2014

(30) Foreign Application Priority Data

Jul. 8, 2011 (ES) .................................. 201131164

(51) Int. Cl.
C07K 16/00 (2006.01)
C07K 14/805 (2006.01)
A23J 1/06 (2006.01)
A23J 3/32 (2006.01)
A23J 3/34 (2006.01)
A23K 1/04 (2006.01)
A23K 1/16 (2006.01)
A23K 1/18 (2006.01)
A23L 1/305 (2006.01)
A23K 1/165 (2006.01)

(52) U.S. Cl.
CPC .................. *C07K 14/805* (2013.01); *A23J 1/06* (2013.01); *A23J 3/32* (2013.01); *A23J 3/34* (2013.01); *A23K 1/04* (2013.01); *A23K 1/1631* (2013.01); *A23K 1/1634* (2013.01); *A23K 1/1656* (2013.01); *A23K 1/1806* (2013.01); *A23K 1/1813* (2013.01); *A23L 1/3053* (2013.01)

(58) Field of Classification Search
None
See application file for complete search history.

(56) References Cited

U.S. PATENT DOCUMENTS

| 3,391,001 | A | * | 7/1968 | Sair | ............................. 426/656 |
| 5,607,840 | A | * | 3/1997 | Van Gorp et al. | ............ 435/68.1 |
| 5,928,686 | A | * | 7/1999 | Ivey et al. | ......................... 426/2 |
| 2004/0142017 | A1 | | 7/2004 | Luebbers | |
| 2010/0239709 | A1 | | 9/2010 | Lamb et al. | |

FOREIGN PATENT DOCUMENTS

| WO | WO 97/39641 | 10/1997 |
| WO | WO 02/11556 | 2/2002 |
| WO | WO 02/19836 | 3/2002 |

OTHER PUBLICATIONS

Net absorption and utilization of nitrogenous compounds across ruminal, intestinal, and hepatic tissues of growing beef steers fed dry-rolled or steam-flaked sorghum grain, J Anim Sci 2002, 80:525-532.*
Gomes (Use of small ruminants milk supplemented with available nitrogen as growth media for Bifidobacterium lactis and Lactobacillus acidophilus, Journal of Applied Microbiology, 1998, 85, 839-848.*
Clark (Microbial Protein Synthesis and Flows of Nitrogen Fractions to the Duodenum of Dairy Cows, Symposium: Nitrogen Metabolism and Amino Acid Nutrition in Dairy Caitle, 1992 J Dairy Sci 75:2304-2323).*
International Search Report for International Application No. PCT/ES2012/000188, mailed Jan. 23, 2013.
Written Opinion of the International Searching Authority for International Application No. PCT/ES2012/000188.
Apr. 10, 2013 Written Reply to Written Opinion of the ISA.

* cited by examiner

*Primary Examiner* — Jeanette Lieb
(74) *Attorney, Agent, or Firm* — Staas & Halsey LLP

(57) ABSTRACT

A nutritional supplement, a method for increasing the bacterial mass in the rumen of a ruminant and a nutritional preparation and corresponding uses. A nutritional supplement including proteins with a degree of hydrolysis above 28% and/or which have more than 23 mg α-amino nitrogen per gram of protein and/or have more than 10% of free amino acids. The hydrolyzed proteins are animal proteins, preferably hemoglobin. The supplement is supplied orally, included in a nutritional preparation, in liquid, concentrated or dehydrated form. The supplement is the basis for a method of increasing the bacterial mass in the rumen of a ruminant in which there is added to the ruminant's diet a supplement with these hydrolyzed proteins

19 Claims, 7 Drawing Sheets

NUTRITIONAL SUPPLEMENT, METHOD FOR INCREASING THE BACTERIAL MASS IN THE RUMEN OF A RUMINANT AND NUTRITIONAL PREPARATION AND CORRESPONDING USES

This application claims the benefit under 35 U.S.C. Section 371, of PCT International Application No. PCT/ES2012/000188, filed Jul. 6, 2012 and Spanish Patent Application No. P201131164 filed Jul. 8, 2011, the contents of which are incorporated herein by reference.

FIELD OF THE INVENTION

The invention relates to a nutritional supplement and to a method for increasing the bacterial mass in the rumen of a ruminant. The invention also relates to a nutritional preparation and to uses of the supplement according to the invention.

STATE OF THE ART

It is deemed beneficial to maximize the synthesis of microbial proteins in the rumen because the amino acid profile of the bacterial proteins is very similar to the amino acid profile required by the host animal, in comparison with the majority of the proteins used as nutrition (NRC, 2001). The rumen microorganisms attain their nitrogen requirements for the synthesis of proteins from a mixture of ammonia, free amino acids and peptides. A large proportion of the digestible diet of a ruminant is converted to the end products by way of microbial fermentation, basically volatile fatty acids (VFA), and the majority of the protein is converted to microbial protein.

Since the bacterial amino acid profile is usually of a better quality than the proteins used as nutrition, the objective in the nutrition of ruminants is to maximize the bacterial growth to promote the synthesis of microbial proteins. The bacterial growth has to be sustained with carbohydrates and nitrogen sources. It has been shown that the bacterial growth is increased with the addition of amino acids and/or peptides, both in the case of cellulolytic bacteria and amylolytic bacteria (Maeng and Baldwin, 1976; Argyle and Baldwin, 1989; Kernick, 1991). It has also been described that fiber digestion is increased with the addition of amino acids (Griswold et al., 1994; Carro and Miller, 1999) and proteins (Cruz Soto et al., 1994) to purely cellulolytic bacteria. In turn, Atasoglu et al. (2001) showed, with pure cellulolytic bacteria cultures, that the incorporation of nitrogen in the form of ammonia in microbial cell nitrogen decreases when the proportion of amino acids is increased in the medium, suggesting that the cellulolytic bacteria also use the amino acids, if available. Similar results have been described when the peptide concentrations are increased; although Atasoglu et al. (2001) state that the cellulolytic bacteria prefer to incorporate the nitrogen from the amino acids against the nitrogen from peptides in their cell nitrogen. Nevertheless, in typical peptide and amino acid concentrations in the rumen, approximately 80% of the cell nitrogen is derived from ammoniacal nitrogen. The addition of branch chain amino acids which will ferment as branch chain volatile fatty acids, and the addition of peptides in the rumen fluid increase the fiber digestion, the production of microbial protein and the growth rates (Russell and Sniffen, 1984; Thomsen, 1985).

The increase of the rumen microbial mass improves the milk production yield (NRC, 2001). As already stated above, it is a common practice in the dairy industry to provide amino acid, peptide or yeast supplements to increase bovine milk production. From among the different peptides used, triptone (which is the peptide obtained from the hydrolysis of casein with the enzyme trypsin) is taken as the reference standard for the addition of nitrogen for bacteria under laboratory conditions.

The majority of animal and vegetable proteins can be hydrolyzed either by enzymatic or acid methods. The enzymatic methods are usually the preferred methods, since no acid residue remains and the amino acids retain their L form.

The use of spray dried hemoglobin (SDH) and dried blood in the dairy industry is well known as a source of proteins which are not hydrolyzed in the rumen and reach the small intestine intact, where they may be digested by the intestinal microflora for the maintenance of the intestinal passage. Nevertheless, they are not used as a protein source to increase the rumen bacterial mass.

SUMMARY OF THE INVENTION

It is an object of the invention to provide a nutritional supplement including hydrolyzed proteins having a high degree of hydrolysis. The hydrolyzed proteins preferably have a degree of hydrolysis above 28% and/or have more than 23 mg of $\alpha$-amino nitrogen per gram of protein and/or have more than 10% of free amino acids.

In fact, as will be shown hereinafter, the in vitro studies, according to the Tilley Terry process, performed on rumen contents, it has been found, surprisingly, that only when high hydrolyzed hemoglobin was added to the rumen medium was there a greater special stimulation in the growth of both Gram-positive and Gram-negative bacteria. With the use of hemoglobin hydrolyzed only to a medium level or unhydrolyzed complete hemoglobin or triptone or yeast, no similar effect was achieved in the rumen bacterial growth. The justification of this improvement is not clearly known. The fact of providing high hydrolyzed protein may possibly imply supplying an amino acid, peptide and/or oligopeptide profile much more varied and more adapted to the needs of the rumen bacterial mass than in the case of providing specific amino acids or peptones (as in the case of the supply of triptone or of the few free amino acids that are synthesized industrially at affordable prices for these applications).

The hydrolyzed proteins are preferably animal proteins, preferably blood proteins and most preferably, hemoglobin.

A further object of the invention is a nutritional preparation for animals, preferably for ruminants, comprising a supplement according to the invention.

Yet a further object of the invention is a method for increasing the bacterial mass in the rumen or belly of a ruminant comprising the step of adding high hydrolyzed proteins in the ruminant's diet. Preferably the hydrolyzed proteins have a degree of hydrolysis in excess of 28% and/or have more than 23 mg of $\alpha$-amino nitrogen per gram of protein and/or more than 10% of free amino acids.

Preferably the hydrolyzed proteins are supplied as a supplement in the animals' diet, preferably that of ruminant animals. Advantageously, there is supplied an amount of said supplement equivalent to between 0% and 25% of the animal's feed portion, preferably said amount is equivalent to between 1% and 10% of the animal's feed portion. The supplement may be added advantageously to the animals' feedstuff, i.e., it is for oral consumption. It may be administered in liquid, concentrated or dehydrated form. If they are supplied dehydrated, the dehydration is preferably carried out by spray drying, although it may also be advantageously done by freeze-drying, in a flash dryer or in a disc dryer.

Advantageously the supplement is supplied to an animal of the group formed by cows, sheep, goats, horses and llamas, preferably dairy cows.

The proteins may be animal or vegetable. Preferably they are blood proteins and most preferably hemoglobin proteins.

Advantageously the hydrolyzed proteins are obtained from hemoglobin originating from the group formed by porcine, bovine, ovine, equine and avian proteins.

A further object of the invention is the use of a nutritional supplement according to the invention to increase the bacterial mass in the rumen of a ruminant, in particular to increase the Gram-negative bacterial mass and/or to increase the milk production of an animal of the group formed by cows, sheep, goats, horses and llamas, preferably dairy cows.

BRIEF DESCRIPTION OF THE DRAWINGS

Further advantages and features of the invention will be appreciated from the following description, in which, without any limiting nature, there is disclosed preferred embodiments of the invention, with reference to the accompanying drawings, in which.

DETAILED DESCRIPTION OF EMBODIMENTS OF THE INVENTION

Example 1

Production of Hydrolyzed Animal Hemoglobin Products

Figure 1:
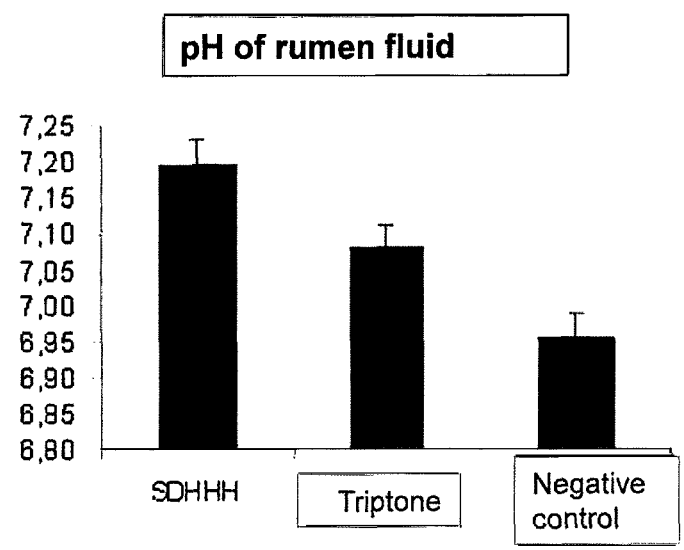
FIG. 1 shows the rumen fluid pH influenced by the supplied nitrogen source.

Generally speaking, the hydrolyzed proteins may be obtained by enzymatic hydrolysis, acid hydrolysis or alkaline hydrolysis.

In the case of enzymatic hydrolysis, it is preferably carried out with enzymes of the group of proteases which are advantageously added in an enzyme amount below 25 wt % of the protein to be hydrolyzed. Preferably the enzymatic hydrolysis is carried out at a pH ranging from 2 to 12.

In the case of acid hydrolysis, it is preferably carried out with an acid of the group formed by sulfuric acid, hydrochloric acid, nitric acid and phosphoric acid. It is advantageously carried out at a temperature above 60° C.

In the case of alkaline hydrolysis, it is preferably carried out with an alkali of the group formed by sodium hydroxide and potassium hydroxide and is advantageously carried out at a temperature above 60° C.

To perform this Example 1, hemoglobin was used as the raw material to be hydrolyzed and the hydrolysis was enzymatic.

Animal hemoglobin may be hydrolyzed by releasing the hemoglobin from the red cells using a pressure pump or other different methods such as dilution with water, high speed stirring, etc. Thereafter, the hemoglobin may be enzymatically hydrolyzed using a proteolytic enzyme under controlled pH and temperature conditions. With the use of enzymatic hydrolysis, a man of the art can obtain the desired degree of hydrolysis. Once a desired degree of hydrolysis has been attained in the hemoglobin, this may be supplied directly as nutrition to the ruminants, may be concentrated and stored as such concentrate, or may be dehydrated by various known methods.

In the case of Example 1, the process followed was as given below:

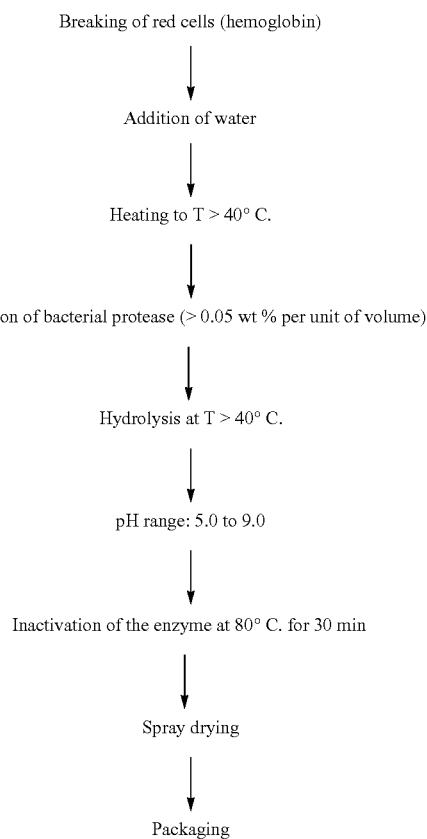

The degree of hydrolysis using this process may vary depending on the temperature, the pH, the dose or amount of enzyme supplied and the reaction time. It was possible to produce the following products in this way:

TABLE 1

Hydrolyzed and spray dried hemoglobin samples obtained and comparison with triptone

| PARAMETERS | Y010514 | 11XIP007-4 | 11XIP007-2 | Y206024 | Triptone |
|---|---|---|---|---|---|
| Degree of hydrolysis | high | high | medium | High | medium |
| Degree of hydrolysis (%) | 37 | 36.3 | 24.5 | | 27.9 |
| N-α-amino (mg/g protein) | 30.75 | 30.2 | 22.8 | 34.62 | 21.6 |
| % free amino acids | 16.3 | 15.3 | 9.6 | 21.58 | 9.1 |
| % Dry material | 99.3 | 95.0 | 93.8 | 96.9 | 96.7 |
| % Nitrogen | 14.30 | 14.04 | 14.33 | 13.9 | 13.10 |
| % Ashes | 11.6 | 13.6 | 11.7 | 12.9 | 4.9 |

Example 2

Tilley Terry Incubation

Rumen samples from three different animals were incubated for 12 hours following the Tilley Terry (1963) process. The fresh rumen fluid was diluted with a buffer solution and a mineral solution at a rate of 10:40 (rumen fluid:buffer-mineral solution) and the nitrogen source was added. Three different treatments were applied to the rumen samples: negative control (no addition of the nitrogen source), 2% triptone (as positive control) and spray dried high hydrolyzed hemoglobin SDHHH, sample Y010514 obtained in the previous Example 1, supplied at a rate (2.1%) providing the same amount of nitrogen as 2% of triptone. The method consisted of incubating the rumen fluid in 100 ml flasks under a $CO_2$ atmosphere at 39° C. for 12 hours.

After 12 hours incubation, a liquid sample was obtained for pH and bacterial growth determination. The pH was determined using an electronic probe.

total microbial DNA was extracted using the RBB+C method that uses the so-called "bead beating" technique in the presence of high concentrations of sodium dodecylsulfate (SDS), salt and EDTA, with the subsequent purification of the DNA being made with QIAamp columns (QIAGEN) (Yu and Morrisson, 2004).

The quantitative RT-PCR was carried out using 96 well 0.2 ml plates and an IQ™ SYBR® Green Supermix with the BioRad MyIQ™ real time detection system. For the bacterial quantification primers specific for regions of the gene 16S rRNA were used, at a final concentration of 0.5 μM. The PCR amplification cycles are given in Table 2. The specificity of the amplicon (a piece of DNA formed as an amplification product) was determined with the analysis of the PCR end product fusion curves by means of the temperature increase at a rate of 0.5° C./30 sec from 55° C. to 95° C. PCR reactions were made in triplicate. Water was used as negative control and the expression was calculated as a standardized relative quantification with the negative control with 2ΔCt.

TABLE 2

Primers and RT-PCR amplification cycles

| Gene | Primers | | Reference | RT-PCR Cycle |
|---|---|---|---|---|
| 16SrRNA Gram-negative | Fw Rv | 5'-AYGACGTCAAGTCMTCATGG-3' 5'-AGGAGGTGATCCAACCGCA-3' | (Klausegger et al., 1999) | 1 × (95° C. 05:00 min) 40 × (95° C. 00:30 min, 65° C. 00:30 min, 72° C. 00:10 min) 1 × (72° C. 00:30 min.) |
| 16SrRNA Gram-positive | Fw Rv | 5'-GAYGACGTCAARTCMTCATGC-3' 5'-AGGAGGTGATCCAACCGCA-3' | (Klausegger et al., 1999) | 1 × (95° C. 05:00 min) 40 × (95° C. 00:30 min, 65° C. 00:30 min, 72° C. 00:10 min) 1 × (72° C. 00:30 min.) |

Determination of Microbial Growth

Since it is not possible to make optical density measurements in rumen fluid, the bacterial growth was estimated using two different methods:
1) Centrifugation and mass determination of a microbial pellet at the end of the twelve hour incubation period,
2) The liquid sample obtained from the incubation flasks was used to extract DNA, and thereafter quantitative RT-PCRs (real time polymerase chain reactions) were performed to determine the total of Gram-positive and Gram-negative bacteria.

For the DNA extraction, the rumen samples were centrifuged after incubation at 6500 g for 15 minutes at 4° C. The supernatant was discarded. The pellet was split into 0.25 g equal parts and frozen (−80° C.) until the later analysis. The pH Measurement In all cases the rumen fluid showed a slight increase in pH at the end of incubation (see FIG. 1). The increase was significantly greater in the case of SDHHH (spray dried high hydrolyzed hemoglobin). The pH increase indicates that the microorganisms were able to use the supplied nitrogen sources as energy sources, causing a release of ammonia.

Microbial Quantification by RT-PCR

Figure 2:
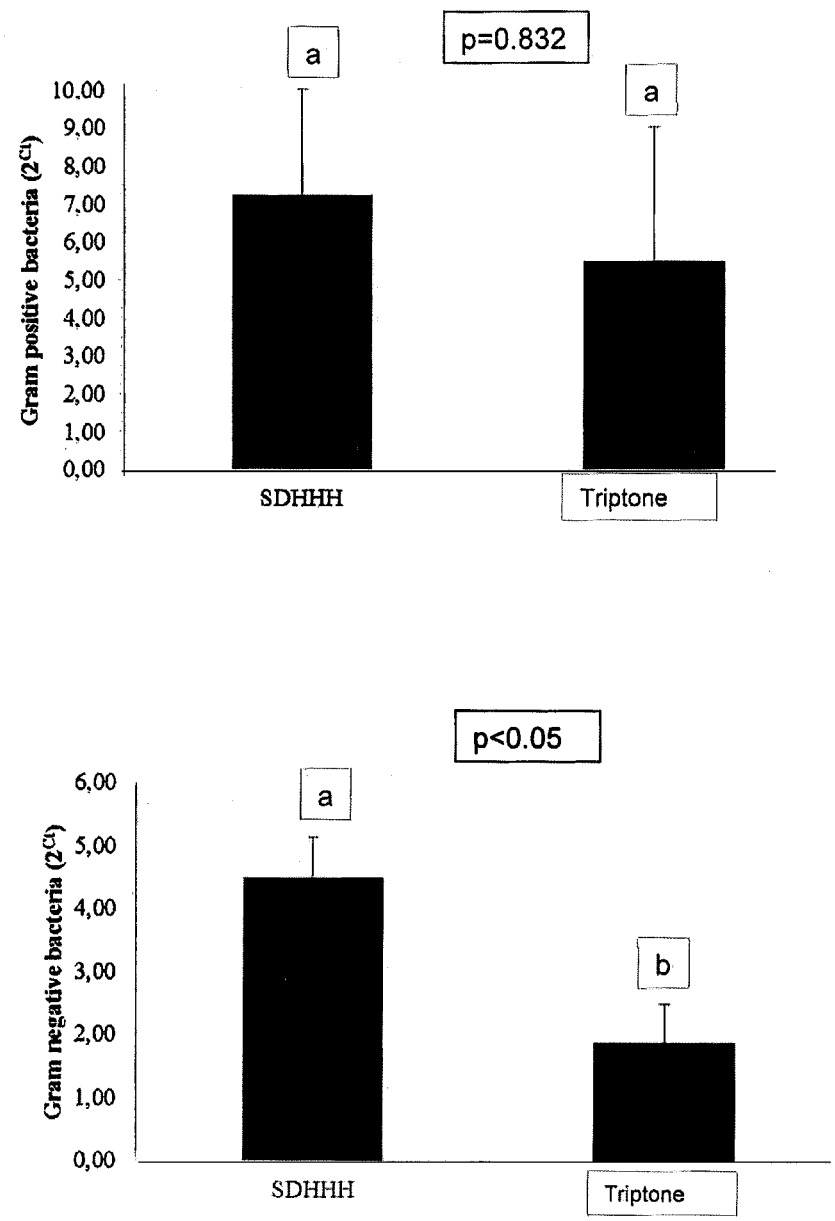
FIG. 2 shows the relative abundance of Gram-positive and Gram-negative bacteria influenced by the supplied nitrogen source in vitro.

FIG. 2 shows the results of the quantitative RT-PCR expressed as $2^{Ct}$ using the negative control as reference (since it is not possible to make an absolute quantification). It is to be seen that the stimulation in the bacterial growth is even more accentuated in the Gram-negative bacteria than in the Gram-positive bacteria.

A comparative study has shown that the peptides are incorporated in a more effective way in the bacterial protein. One hypothesis to explain why the growth of the Gram-negative bacteria is greater than the growth of the Gram-positive bacteria could be based on the special composition of oligopeptides, peptides and free amino acids present in the nitrogen source.

Therefore, it may be seen that SDHHH is an easily available nitrogen source for the microbial protein synthesis. Additionally, SDHHH seems preferably to stimulate the growth of the Gram-negative bacteria, that are, more desirable than the Gram-positive bacteria in the rumen.

Example 3

4 Tilley Terry incubation replicates were made, each of them using three different rumen liquid samples from three different cows to determine the rumen fermentation and the microbial changes, compared with a control to which no nitrogen source had been added. The supplied nitrogen sources were:
plasma
spray dried medium hydrolyzed hemoglobin, SDMHH (sample 11XIP007-2 of Example 1)
spray dried high hydrolyzed hemoglobin (SDHHH) (sample 11XIP007-4 of Example 1)
98% urea
soybean nutrient (SBM)
yeast
spray dried red blood cells (RBC)

The rumen liquids were diluted at a rate of 10:40 and 1% of maize flour was added thereto (including the control). All the protein sources were supplied in an amount such as to provide 2% nitrogen.

The incubation lasted for 16 hours, under continuous stirring (150 rpm), 5% $CO_2$ and 39° C.

The pH was measured at the start and at the end of incubation, and the concentration of Gram-negative and Gram-positive bacteria was determined.

Figure 3:
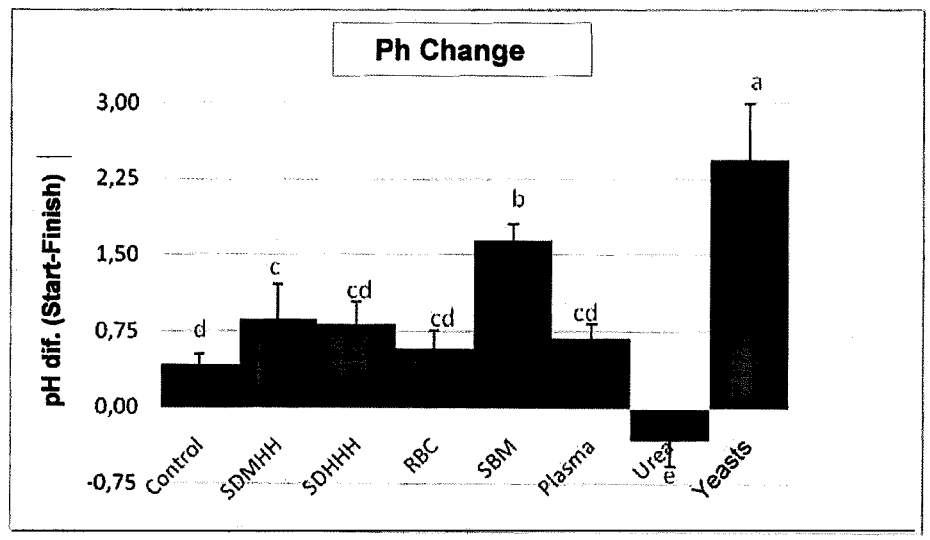
FIG. 3 shows the pH variation in each of the incubations of Example 3.

FIG. 3 shows the variation of pH in each incubation.

Figure 4:
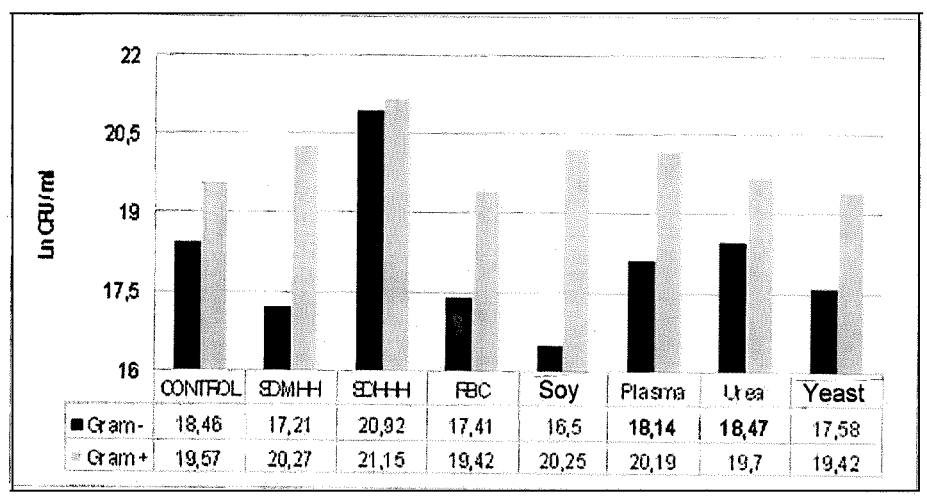
FIG. 4 shows the bacterial count of Example 3.

FIG. 4 shows the bacterial count.

Both SDHHH and SDMHH are seen to produce a positive effect in the increase of rumen pH, as also happens with the yeast, the SBM and the plasma. Nevertheless, surprisingly, the SDHHH shows a superior effect in the growth of both Gram-positive and Gram-negative rumen bacteria. This effect is not to be seen either with SDMHH or with the unhydrolyzed hemoglobin.

Example 4

The objective was to evaluate the effects of a protein hydrolysate on rumen fermentation, milk production, milk composition, and urea, glucose, and insulin blood concentrations The experiment was a replicated parallel complete randomized experiment with two treatments, 16 cows, during 30 days. The experimental unit was the cow (treatments were applied on an individual basis).
Animals and Treatments Sixteen cows were fed a common TMR (total mixed ration) which was sampled and analyzed for dry matter (DM), crude protein (CP), neutral detergent fiber (NDF), non-fiber carbohydrates (NFC), starch, and ether extract (EE) on a weekly basis. There were two treatments (8 cows per treatment): a control group that received 100 g of urea/d, and a group (SDHHH group or APC group) that received 319 g of SDHHH/d (sample Y206024 obtained in example 1, the SDHHH is internally named as peptein-4 by APC). These two compounds were mixed in water and then mixed with the TMR.

The Data of the Used SDHHH are:
Moisture 3.1%
Protein 87.1%
Ashes 12.9%
Free amino acids 21.58%
Free α-amino nitrogen 34.62 mg/g protein Cows were fed twice daily. The two treatments supplied the same amount of supplemental N (44.8 g/d). There were 8 rumen-cannulated cows, 4 in each treatment that were used to obtain rumen samples.
Measurements Individual intake and eating behavior was monitored automatically using a feed intake monitoring system (Bach et al., 2004). Milk production was collected throughout the study. In addition, on days 0, 14, and 28 d, all cows were sampled for milk components (fat, protein, lactose, urea and somatic cell counts) at both AM and PM milkings.

Also, cannulated animals were used to collect rumen samples on days 0, 14, and 28 at 0, 2, 4 and 6 h after the morning feeding to determine concentration of volatile fatty acids, pH, and ammonia. In addition, all rumen samples were processed and stored at −80 C for subsequent DNA extraction and quantification of Gram positive and Gram negative bacteria, and protozoa. For DNA extraction, rumen samples were centrifuged post-incubation at 6500×g during 15 min at 4° C. The supernatant was discarded and the homogenized pellet distributed in 0.25 g aliquots that were frozen at −80° C. until used. Total microbial DNA was extracted using the RBB+C method which employs bead beating in the presence of high concentrations of sodium dodecyl sulphate (SDS), salt and EDTA, and subsequent DNA purification with QIAamp columns (QIAGEN) (Yu and Morrisson, 2004).

Figure 5:
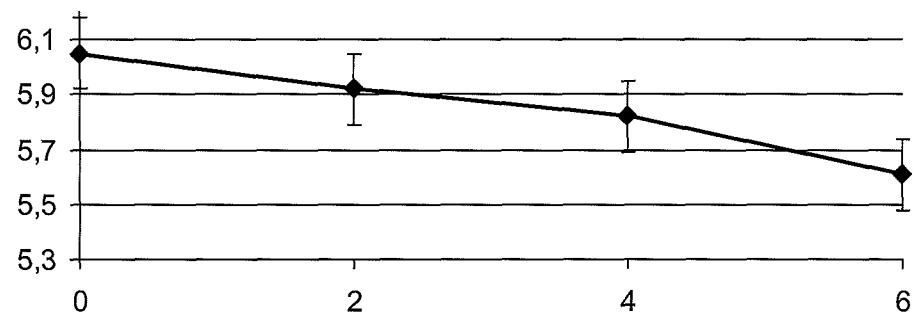
FIG. 5 shows the evolution of rumen pH with respect to feeding time of Example 4.

Quantitative RT-PCR was performed using 0.2 ml 96 well plates and IQ™SYBRO® Green Supermix with the MyIQ™ Real-Time Detection system from BioRad. For bacteria quantification, specific primers for regions of 16S rRNA gene were used at 0.5 µM final concentration. Amplicon specificity was assessed via melting curve analyses of the PCR end-products by increasing the temperature at a rate of 0.5° C./30 sec from 55° C. to 95° C. PCR reactions were carried out in triplicates. Water was used as negative control and expression was calculated as relative quantification normalized to the negative control by 2ΔCt.
Data Processing and Statistical Analysis The experimental unit was the cow. Data were analyzed with a 2-level random effects model. The fixed parts of the models accounted for treatment, time, and their two-way interaction. The error term for all models was cow nested within treatment.
Results Average rumen pH was 5.93 and 5.81±0.10 for Control and SDHHH cows, respectively, with difference being not significant (P=0.47), and as expected, rumen pH changed according to sampling time (FIG. 5).

Figure 6:
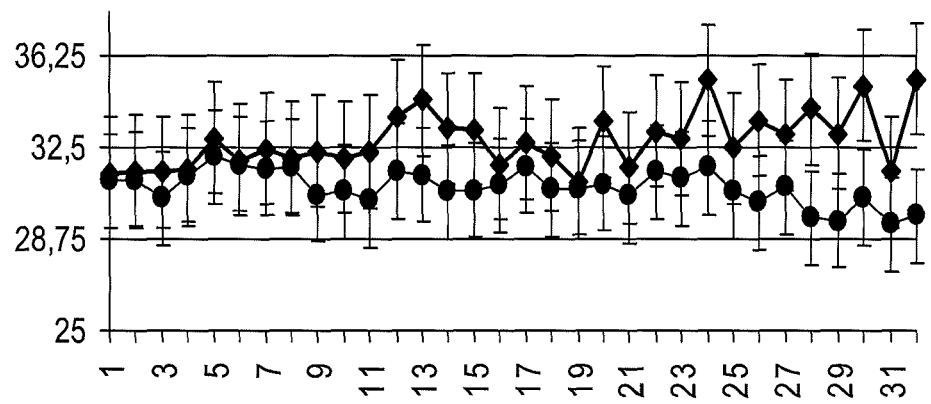
FIG. 6 shows the evolution of milk production (kg/d) as affected by treatment and days on treatment of Example 4.
Figure 7:
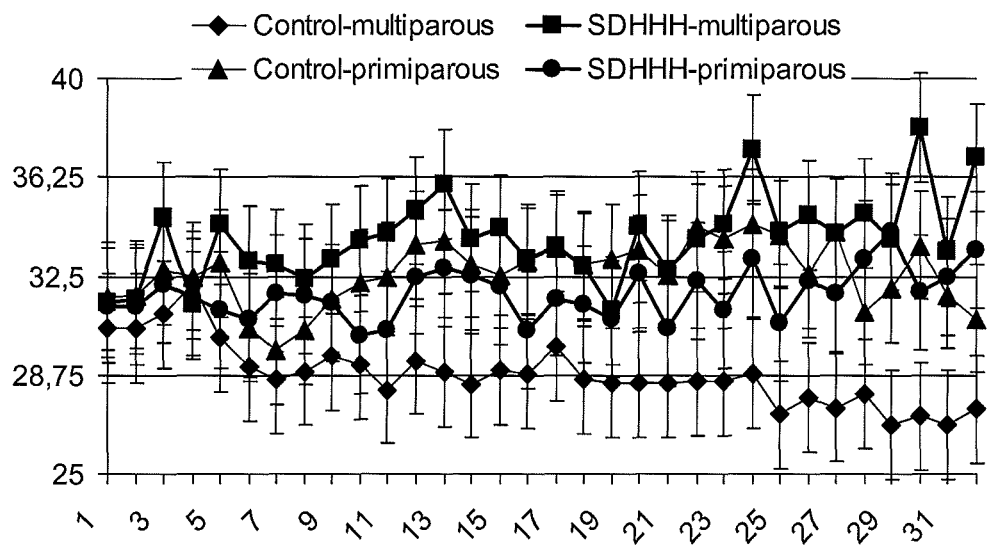
FIG. 7 shows the evolution of milk production (kg/d) as affected by treatment, parity, and days on treatment of Example 4.
Figure 8:
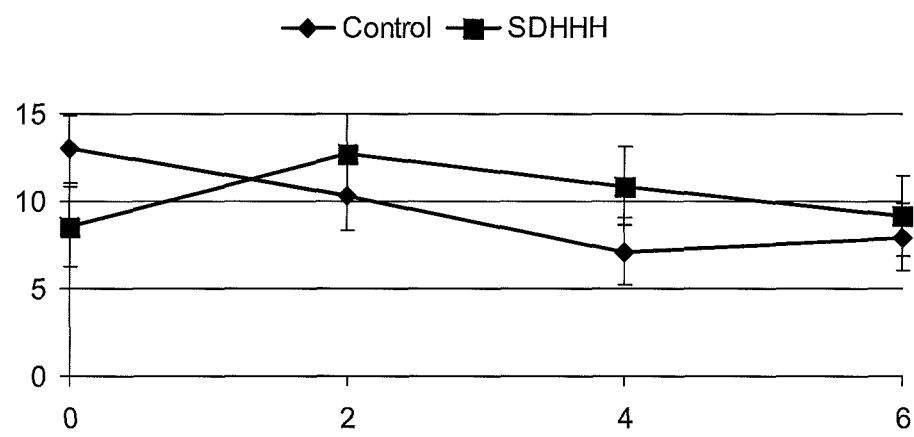
FIG. 8 shows the evolution of rumen ammonia nitrogen (mg/dl) as affected by treatment and days on treatment of Example 4.

Milk production was, as a whole, not affected by treatment (Table 3); however there was an interaction between treatment and days on treatment (FIG. 6) and a triple interaction between parity, treatment, and days on treatment (FIG. 7). Basically, after about 7-10 days on treatment, SDHHH cows started to produce more milk than cows on Control. Interestingly, multiparous cows responded much better than primiparous cows to SDHHH supplementation (FIG. 7). Overall, milk production from primiparous cows on Control was 32.5 kg/d, and those in SDHHH was 31.7 kg/d; whereas multiparous cows on Control produced 27.9 kg/d and those in SDHHH produced 33.6 kg/d. Rumen ammonia concentrations did no differ between treatments, and it was 10.42±1.26 mg/dl for control and 10.63±1.09 mg/dl for SDHHH cows. However, the evolution of rumen ammonia concentrations after the morning feeding was different (P<0.02) between treatments (FIG. 8). Basically, SDHHH cows had lower NH3 concentrations at feeding time, and then they increased and were maintained above the concentrations for the Control cows until 4 hours post-feeding. These results would suggest an improved availability of N in the rumen of SDHHH cows compared to Control. Dry matter intake was not affected by treatment, although it decreased over time in SDHHH cows. This was probably due to the low (P<0.05) eating rate in SDHHH compared to Control cows (Table 3). Feed efficiency tended to increase with SDHHH, and it increase as days on treatment increased (Table 3).

TABLE 3

Dry matter intake (DMI), feeding behavior, and milk production as affected by treatment and days on treatment.

| | Treatment | | | P value | | | TreatxDay |
|---|---|---|---|---|---|---|---|
| Item | Control | SDHHH | SE | Treatment | Day | TreatxDay | xParity |
| Milk yield, kg/d | 29.6 | 30.3 | 1.03 | 0.39 | <0.001 | 0.005 | 0.001 |
| DMI, kg/d | 21.6 | 20.3 | 0.72 | 0.23 | <0.001 | 0.002 | 0.39 |
| Eating time, min/d | 170 | 174 | 3.27 | 0.39 | 0.02 | 0.02 | 0.77 |
| Eating rate, g/min | 128.8 | 118.3 | 3.2 | 0.04 | 0.001 | 0.15 | 0.88 |
| Fat, % | 3.42 | 3.68 | 0.22 | 0.47 | 0.39 | 0.65 | 0.95 |
| Protein, % | 3.32 | 3.30 | 0.10 | 0.25 | 0.44 | 0.41 | 0.56 |
| Lactose, % | 4.92 | 4.96 | 0.03 | 0.36 | 0.68 | 0.31 | 0.54 |
| Urea, mg/L | 255.8 | 241.6 | 15.02 | 0.52 | 0.03 | 0.27 | 0.32 |
| SSCC, $10^3$ cel/ml | 179.7 | 135.8 | 31.18 | 0.34 | 0.31 | 0.15 | 0.45 |
| Milk effic., kg/kg | 1.37 | 1.49 | 1.56 | 0.13 | <0.001 | <0.001 | 0.54 |

Milk fat was not affected by treatment. (Table 3). However, there was a significant interaction between treatment and parity (P<0.01). Primiparous cows on control treatment had 2.75% fat, whereas primiparous cows on SDHHH treatment had 3.96% fat. This increase in milk fat could be the reason why primiparous cows did not produced more milk with SDHHH as it occurred with multiparous cows. On the other hand, multiparous cows on the Control treatment had 4-10% butter fat, and multiparous cows on SDHHH had 3.38% milk fat. Again, these results could explain, in part, the increase in milk yield observed in multiparous cows on SDHHH compared to those on Control. Milk protein content was no affected by treatment or any interaction. Lactose was not affected by treatment either, although primiparous cows had greater values (P<0.01) than multiparous cows (5.02 vs 4.86±0.03%, respectively). Milk urea content was not affected by treatment, also it progressively increased as days on experiment increased (P<0.05) in both treatments.

Somatic cell counts in milk were not affected by treatment either (Table 3).

Figure 9:
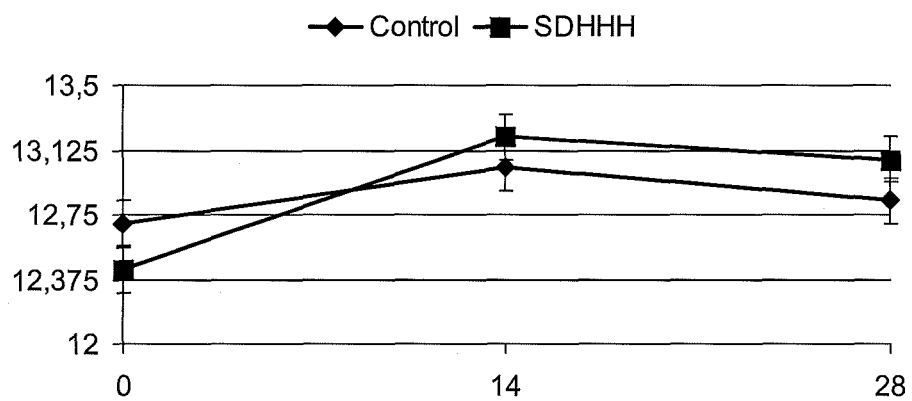
FIG. 9 shows the evolution of Gram positive bacteria (Ct) in the rumen as affected by treatment and days on treatment of Example 4.
Figure 10:
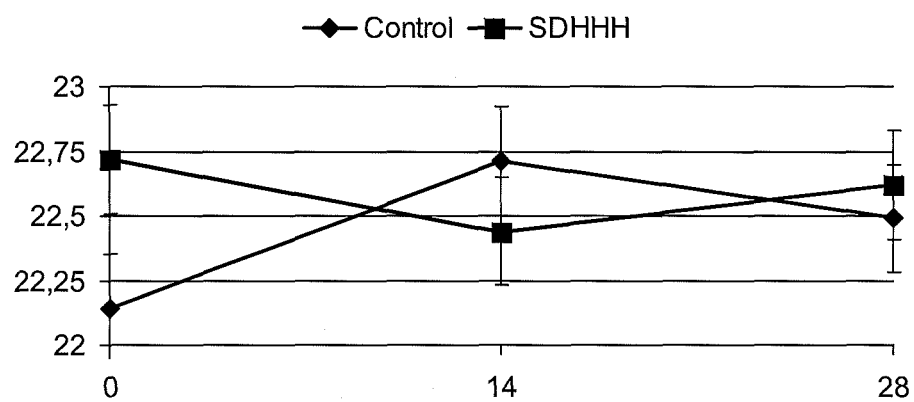
FIG. 10 shows the evolution of Gram negative bacteria (Ct) in the rumen as affected by treatment and days on treatment of Example 4.

The rumen concentration of Gram positive bacteria tended (P=0.07) to decrease in SDHHH compared with Control cows as days on treatment increased (FIG. 9, the greater the Ct, the lower the concentration of rumen bacteria). Decreasing the proportion of Gram positive bacteria is desirable. More interestingly, Gram negative bacteria in the rumen increased (P<0.05) as days on SDHHH treatment increased, whereas cows in the Control treatment decreased (FIG. 10). However, no differences were detected between treatments along the sampling day (at 0, 2, 4, and 6 h post-feeding), neither for Gram positive, nor for Gram negative bacteria.

Figure 11:
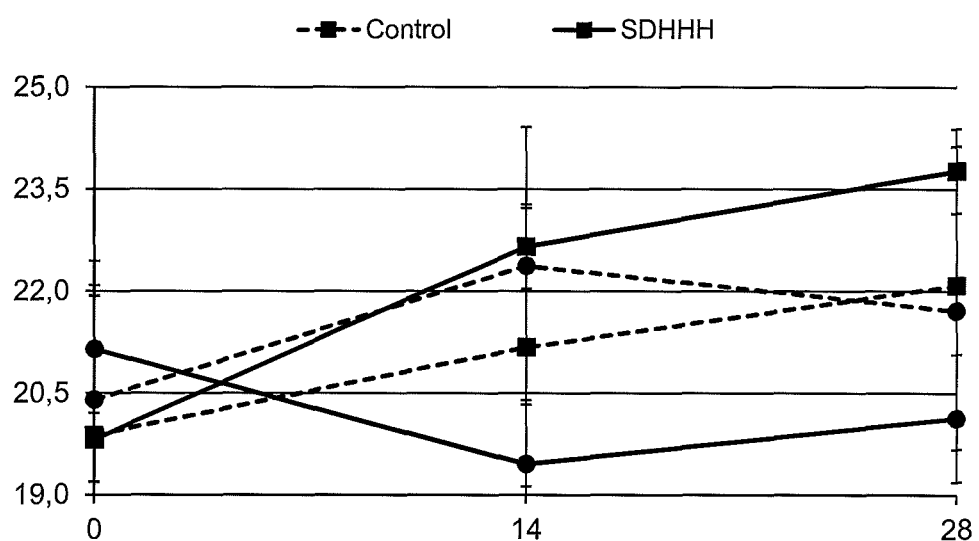
FIG. 11 shows the evolution of protozoa counts (Ct) as affected by treatment, parity, and days on treatment of Example 4. Low Ct means high counts. Squares represent multiparous cows and circle primiparous cows.

Last, protozoa counts tended to be lower (P=0.08) in multiparous cows receiving SDHHH than in multiparous cows in the Control treatment (Ct=22.07 vs 21.04±0.27, respectively; remember that greater Ct means less counts). Also, the evolution of protozoa counts was different (P<0.05) in multiparous than in primiparous depending on treatment (FIG. 11). Basically, in multiparous cows on SDHHH, as days on treatment increased, the number of protozoa decreased, whereas in primiparous cows on SDHHH, the number of protozoa increased over time. In fact, ignoring the data from day zero, overall, primiparous cows on Control had 20.82 Ct, and those in SDHHH had 19.79 Ct (more protozoa), and multiparous cows in Control had 21.62 Ct, and those in SDHHH had 23.2 Ct (less protozoa), and this interaction was significant at P<0.01.

CONCLUSIONS

These results show that supplementing multiparous cows with SDHHH increases milk production after about 7-10 days of treatment. This increase in milk yield is accompanied by a decrease in milk fat content. In primiparous cows there was no increase in milk yield, but milk fat content increased when cows were supplemented with SDHHH. Supplementation of SDHHH lowers NH3 concentration at feeding time, but increases it above the concentrations for the Control cows until 4 h post-feeding. These results would suggest an improved availability of N in the rumen of SDHHH cows compared to Control for at least the first 4 h post-feeding.

The rumen concentration of Gram positive bacteria tend to decrease in SDHHH compared with Control cows as days on treatment increase. More interestingly, Gram negative bacteria in the rumen increase as days on SDHHH treatment increase. However, no differences were detected between treatments along the sampling day (at 0, 2, 4, and 6 h post-feeding), neither for Gram positive, nor for Gram negative bacteria.

These results confirm the findings from in vitro studies that suggest that SDHHH foster growth of Gram negative bacteria in the rumen. Furthermore, it seems that SDHHH decreased protozoa numbers in multiparous (which should improve protein utilization), but not in primiparous cows.

REFERENCES

Argyle, J. L., and R. L. Baldwin. 1989. Effects of amino acids and peptides on rumen microbial growth yields. J. Dairy Sci. 72:2017.

Atasoglu, C., C. J. Newbold, and R. J. Wallace. 2001. Incorporation of [15N]ammonia by cellulolytic ruminal bacterial *Fibrobacter succinogenes* BL2, *Ruminococcus albus* SY3, and *Ruminococcus flavefaciens* 17. Appl. Environ. Microbiol. 67:2819-2822.

Bach A., C. Iglesias, and I. Busto. 2004. Technical note: a computerized system for monitoring feeding behavior and individual feed intake of dairy cattle. J. Dairy Sci. 87:4207-4209.

Carro, M. D., and E. L. Miller. 1999. Effect of supplementing a fibre basal diet with different nitrogen forms on ruminal fermentation and microbial growth in an in vitro semi-continuous culture system (RUSITEC). BJN 82:149.

Cruz Soto, R., S. A. Muhammed, C. J. Newbold, C. S. Stewart, and R. J. Wallace. 1994. Influence of peptides, amino acids and urea on microbial activity in the rumen of sheep receiving grass hay on the growth of rumen bacteria in vitro. Anim. Feed Sci. Technol. 49:151-161.

Griswold, K. E., W. H. Hoover, T. K. Miller, and W. V. Thayne. 1996. Effect of form of nitrogen on growth of ruminal microbes in continuous culture. J. Anim. Sci, 74:483.

Klausegger, A., Hell, M., Berger, A., Zinober, K., Baier, S., Jones, N., Sperl, W. & Kofler, B. 1999. Gram type-specific broad-range PCR amplification for rapid detection of 62 pathogenic bacteria. J Clin Microbiol 37, 464-466.

Kernick, B. L. 1991. The effect of form of nitrogen on the efficiency of protein synthesis by rumen bacteria in continuous culture. Ph.D. Dissertation. University of Natal, Pietermaritzburg, South Africa.

Maeng, W. J., and R. L. Baldwin. 1976. Dynamics of fermentation of a purified diet and microbial growth in the rumen. J. Dairy Sci. 59:636.

NRC, 2001 Nutrient Requirements of Dairy Cattle, 7th ed. National Academy Press, Washington, D.C.

Russell, J. B., and C. J. Sniffen. 1984. Effect of carbon-4 and carbon-5 volatile fatty acids on growth of mixed rumen bacteria in vitro. J. Dairy Sci. 67:987.

Thomsen, K. V. 1985. The specific nitrogen requirements of rumen microorganisms. Acta Agric. Scand. Suppl. 25:125.

Tilley, J. M. A. and R. A. Terry. 1963. A two stage technique for the in vitro digestion of forage crops. British Grassland society 18:104-111.

Yu, Z. and M. Morrison. 2004. Improved extraction of PCR-quality community DNA from digesta and fecal samples. BioTechniques 36:808-812.

The invention claimed is:

1. A method for increasing the microbial mass in a rumen of a ruminant, comprising:

selecting a hydrolyzed protein having more than 23 mg α-amino nitrogen per gram of the protein;
selecting the hydrolyzed protein to be a hemoglobin protein; and
adding to a diet of said ruminant the hydrolyzed hemoglobin protein.

2. The method of claim 1, wherein said hydrolyzed protein is supplied as a supplement in animal diets.

3. The method of claim 1, wherein said hydrolyzed protein is supplied as a supplement in ruminant animal diets.

4. The method of claim 2, wherein an amount of said supplement is supplied equivalent to between 0% and 25% of the animal's nutritional portion.

5. The method of claim 2, wherein said supplement is supplied to an animal of the group formed by cows, sheep, goats, horses and llamas.

6. The method of claim 2, wherein said supplement is supplied to dairy cows.

7. The method of claim 1, wherein said hydrolyzed protein is obtained by enzymatic hydrolysis.

8. The method of claim 7, wherein said enzymatic hydrolysis is carried out with enzymes of the group formed by proteases.

9. The method of claim 7, wherein said enzymatic hydrolysis is performed at a pH ranging from 2 to 12.

10. The method of claim 7, wherein in said enzymatic hydrolysis there is added an amount of enzyme of less than 25 wt. % of the protein to be hydrolyzed.

11. The method of claim 1, wherein said hydrolyzed protein is obtained by acid hydrolysis.

12. The method of claim 11, wherein said acid hydrolysis is carried out with an acid of the group formed by sulfuric acid, hydrochloric acid, nitric acid and phosphoric acid.

13. The method of claim 11, wherein said acid hydrolysis is carried out at a temperature of above 60° C.

14. The method of claim 1, wherein said hydrolyzed protein is obtained by alkaline hydrolysis.

15. The method of claim 14, wherein said alkaline hydrolysis is carried out with an alkali of the group formed by sodium hydroxide and potassium hydroxide.

16. The method of claim 14, wherein said alkaline hydrolysis is carried out at a temperature of above 60° C.

17. The method of claim 1, wherein said hydrolyzed protein is added to said ruminant's feed.

18. The method of claim 1, wherein said hemoglobin originates from the group formed by porcine, bovine, ovine, equine and avian.

19. The use of a nutritional supplement comprising:

selecting a hydrolyzed protein having more than 23 mg α-amino nitrogen per gram of protein;
adding the hydrolyzed protein to a diet of a ruminant to increase a Gram-negative bacterial mass in a rumen of the ruminant.

* * * * *